United States Patent
Gott et al.

(12) 
(10) Patent No.: US 6,287,580 B1
(45) Date of Patent: Sep. 11, 2001

(54) COSMETIC COMPOSITIONS WITH SELF-WARMING COMPONENT

(75) Inventors: Robert Edward Gott, Norwalk; Craig Stephen Slavtcheff, Guilford; Alexander Paul Znaiden, Trumbull; Brian Andrew Crotty, Branford, all of CT (US)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/559,218

(22) Filed: Apr. 26, 2000

Related U.S. Application Data

(60) Provisional application No. 60/148,776, filed on Aug. 13, 1999.

(51) Int. Cl.[7] .............................. A61K 6/00; A61K 7/00
(52) U.S. Cl. ..................... 424/401; 424/400; 424/70.1; 424/78.02; 424/78.03; 514/844; 514/873; 514/886; 514/887; 514/946; 514/947
(58) Field of Search .................................. 424/59, 78.02, 424/78.03, 78.05, 78.07, 401, 502

(56) References Cited

U.S. PATENT DOCUMENTS

| | | |
|---|---|---|
| 3,250,680 | 5/1966 | Menkart et al. . |
| 4,199,548 * | 4/1980 | Kaiho .................................. 422/305 |
| 4,626,550 | 12/1986 | Hertzenberg . |
| 4,833,136 * | 5/1989 | Markwell .............................. 514/212 |
| 5,046,479 * | 9/1991 | Usui .................................... 126/204 |
| 5,322,683 | 6/1994 | Mackles et al. . |
| 5,879,378 | 3/1999 | Usui . |

FOREIGN PATENT DOCUMENTS

| | | |
|---|---|---|
| 1079156 | 12/1993 | (CN) . |
| 61251620 | 11/1986 | (JP) . |
| 93/08793 | 5/1993 | (WO) . |

OTHER PUBLICATIONS

NTIS "Pilot Scale On–Site Evaluation of Activated Carbon For Rapid Oxidation of Ferrous Iron in Acid Mine Water", Rhode Island Analytical Labs, Inc.—Oct. 1981.
Sheet on Heat Factory Disposable Warmers—Jul. 22, 1999.
Sheet on Character Warmers—Jul. 22, 1999.
International Search Report.

* cited by examiner

*Primary Examiner*—Thurman K. Page
*Assistant Examiner*—Charesse L. Evans
(74) *Attorney, Agent, or Firm*—Milton L. Honig

(57) ABSTRACT

A self-warming cosmetic composition is provided which delivers skin conditioning agents and is based upon a redox system of iron powder and a catalyst such as charcoal to provide the warmth. The system is activated with moisture and air.

7 Claims, No Drawings

COSMETIC COMPOSITIONS WITH SELF-WARMING COMPONENT

This application claims benefit of Provisional No. 60/148,776 filed Aug. 13, 1999.

BACKGROUND OF THE INVENTION

1. Field of the Invention

The invention concerns cosmetic compositions in the form of strips, patches, skin liquids, creams, gels or pastes which can evolve heat when in contact with moisture.

2. The Related Art

Heat-producing cosmetic compositions produce a very pleasant sensation. These formulations are friendlier than the cold traditional products applied to the skin. Considerable prior technology is available for generating warmth.

U.S. Pat. No. 3,250,680 (Menkart et al.) reports the use of finely divided solid adsorbent materials which are capable of exothermically reacting with water. Illustrative of these materials are silica gel, activated alumina and synthetic zeolites. U.S. Pat. No. 4,626,550 (Hertzenberg) discloses similar heating systems with improved versions of zeolite based on the presence of potassium ions as replacement for some of the sodium ions. A still further elaboration is found in WO 93/08793 (Kemp et al.) reporting on other exothermic agents reactive with water. These include kaolin, Fuller's Earth, china clay and bentonite.

A common problem with the known art is the requirement for very high levels of water reactive solids. Without a significant concentration of those solids, temperature increase will be relatively small. There remains a need for cosmetic compatible systems achieving much higher heat output per gram of heating agent. High levels of solid heating agents have the further problem of thickening the compositions beyond ready flowability.

Accordingly, it is an object of the present invention to provide cosmetic compositions adapted to be self warming which rely upon highly efficient heat generating systems.

Another object of the present invention is to provide cosmetic compositions adapted to be self warming wherein the heating agents are present at levels insufficient to prevent the product from easily flowing.

These and other objects of the present invention will become more readily apparent from consideration of the following summary and detailed discussion.

SUMMARY OF THE INVENTION

A self-warming cosmetic composition is provided which includes:

(i) from about 0.1 to about 99% by weight of a skin conditioning agent; and (ii) from about 0.1 to about 95% by weight of a redox system based upon iron powder and a high surface area catalyst.

DETAILED DESCRIPTION OF THE INVENTION

Now it has been found that highly efficient heating of cosmetic compositions can be achieved by use of iron redox systems. Generated heat can give an aesthetically pleasant sensation to the skin and can assist in delivery of skin conditioning agents to allow their more effective penetration by opening skin pores.

An essential element of the present invention thus is an iron redox system. Central to the system is iron powder. By the term iron powder is meant elemental iron, iron oxides and ferrous salts which can be oxidized to the ferric oxidation state, and combinations thereof. Oxygen is delivered to the system via an aqueous phase to allow mixing with the iron powder. The combination of iron and air is activated by a catalyst. Preferably the catalyst is a substance which increases surface area contact of the reactants. Most preferred is activated charcoal but other high surface area solids may also be useful. Alternative catalysts may be alumina, aluminosilicates, silica and a variety of clays. Although not vital to the reaction, water absorbents such as Vermiculite may be utilized as an inexpensive water reservoir. Vermiculite is an aluminum-iron magnesium silicate. In certain systems salts such as sodium chloride may be employed to further assist the reaction. Certain amounts of water can also be originally present to initiate the heating reaction. Access to air should be limited. Air (and aerated water) initiate the reaction. Cosmetic product dispensers are preferred which seal the product from the atmosphere during storage periods.

Amounts of the iron powder may range from about 0.1 to about 95%, preferably from about 2 to about 50%, more preferably from about 5 to about 30%, optimally from about 10 to about 20% by weight of the cosmetic composition. Amounts of catalyst may range from about 0.01 to about 30%, preferably from about 0.1 to about 10%, optimally from about 1 to about 5% by weight of the cosmetic composition. When present the Vermiculite or equivalent substance may be present from about 0.01 to about 30%, preferably from about 0.1 to about 10%, optimally from about 0.5 to about 3% by weight of the cosmetic composition. Salts when present in the composition may range from about 0.001 to about 15%, preferably from about 0.01 to about 10%, optimally from about 0.5 to about 8% by weight of the cosmetic composition. The weight ratio of iron powder to catalyst may range from about 1000:1 to about 1:1000, preferably from about 100:1 to about 1:1, optimally from about 10:1 to about 2:1.

A second important element is that of a skin conditioning agent. These agents may be selected from emollients, petrolatum, fatty acids, humectants, surfactants, keratolytic agents, retinoids, quaternary ammonium polymers, sunless tanning agents and mixtures thereof.

Collectively the skin conditioning agents will constitute from about 0.1 to about 99%, preferably from about 1 to about 80%, more preferably from about 5 to about 70%, optimally from about 10 to about 30% by weight of the cosmetic compositions.

Emollient materials may serve as skin conditioning agents. These may be in the form of silicone oils and carboxylic esters. Amounts of the emollients may range anywhere from about 0.1 to about 30%, preferably between about 1 and about 20% by weight.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

Fatty acids having from 10 to 30 carbon atoms may also be used as skin conditioning agents for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as skin conditioning agents for compositions of this invention. The humectant aids in increasing the effectiveness of emollients, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Surfactants may also be present in compositions of the present invention. Total concentration of the surfactant may range from about 0.1 to about 40%, preferably from about 1 to about 20%, optimally from about 1 to about 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di- fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Keratolytic agents such as $C_2$–$C_{25}$ alpha-hydroxy carboxylic and beta-hydroxycarboxylic acids and their salts are useful skin conditioning agents of this invention. Illustrative materials are glycolic, lactic, salicylic, alpha-hydroxyoctanoic acids and salts thereof. The salts may be selected from alkalimetal, ammonium and $C_1$–$C_{20}$ alkyl or alkanolammonium counterions. Levels of these keratolytic agents may range from about 0.001 to about 10%, preferably between about 0.2 and about 8%, optimally between about 1 and about 4% by weight.

Retinoids useful as skin conditioning agents may include retinol, retinoic acid and $C_1$–$C_{22}$ esters of retinol such as retinyl palmitate, retinyl acetate and retinyl linoleate. Amounts may range from about 0.0001 to about 1% by weight.

Quaternary ammonium polymers useful as skin conditioning agents include guar hydroxypropyltrimonium chloride available as Jaguar C134S and Polymer JR. Amounts may range from about 0.01 to about 10%, preferably from about 0.1 to about 1% by weight.

Sunless tanning agents useful for this invention include dihydroxyacetone and sugars such as xylitol. Amounts may range from about 0.1 to about 15% by weight.

Thickeners may be utilized as a pharmaceutically acceptable carrier of compositions according to the present invention. Typical thickeners include crosslinked acrylates (e.g. Carbopol 9827), hydrophobically-modified acrylates (e.g. Carbopol 13827), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Minor adjunct ingredients may also be present in the compositions. Among these may be the water-insoluble vitamins such as Vitamin A Palmitate, Vitamin E Acetate and DL-panthenol.

Colorants, fragrances, opacifiers and abrasives may also be included in compositions of the present invention. Each of these substances may range from about 0.05 to about 5%, preferably between 0.1 and 3% by weight.

Cosmetic compositions of the present invention may be in any form. These forms may include emulsified systems such as lotions and creams, microemulsions, roll-on formulations, mousses, ointments (hydrophilic and hydrophobic), aerosol and non-aerosol sprays, strips or patches and pad-applied formulations. When the compositions are impregnated onto a strip, patch or pad, the substrate textile may be a woven or non-woven material of synthetic or natural fiber. Synthetics include polyethylene, polypropylene, polyamide, polyester, polyurethane, rayon and combinations thereof. Natural fibers are cellulosics such as cotton, wood pulp, wool, linen and combinations thereof. Mixed natural and synthetic fibers can be employed. The relative weight ratio of redox system to substrate is about 1:1000 to 5:1, preferably about 1:100 to about 1:50, optimally about 1:30 to about 1:2.

Except in the operating and comparative examples, or where otherwise explicitly indicated, all numbers in this description indicating amounts of material ought to be understood as modified by the word "about".

The following Examples will more fully illustrate embodiments of this invention. All parts, percentages and proportions referred to herein and in the appended claims are by weight unless otherwise indicated.

EXAMPLE 1

A warming facial mask formulation is reported in Table I.

TABLE I

| COMPONENT | WEIGHT % |
| --- | --- |
| PHASE A | |
| Butylene Glycol | 42.00 |
| Hydroxypropyl Cellulose | 0.80 |
| Sodium Magnesium Silicate | 0.50 |
| Phase B | |
| PEG-8 | 4.00 |
| Methyl Gluceth-20 | 0.60 |
| Dimethicone Copolyol | 0.60 |
| Phase C | |
| Iron Powder | 30.00 |
| Charcoal | 7.00 |
| Vermiculite | 3.50 |
| Kaolin | 10.00 |
| Phase D | |
| Fragrance | 0.50 |
| Herbal Extracts | 0.50 |

EXAMPLE 2

An anti-aging skin system based on a retinoid active is reported under Table II.

TABLE II

| COMPONENT | WEIGHT % |
| --- | --- |
| Cyclomethicone | 36.00 |
| Crosslinked Polysiloxane Elastomer in Cyclomethicone (25% Active) | 24.00 |
| Butylene Glycol | 17.50 |
| Iron Powder/Charcoal (4:1 weight ratio) | 10.00 |
| Dimethyl Isosorbide | 2.00 |
| Retinyl Linoleate | 0.50 |
| Cetyl Dimethicone Copolyol | 0.80 |
| Water | Balance |

EXAMPLE 3

This Example illustrates a sunless tanner type formulation details of which are recorded in Table III.

TABLE III

| COMPONENT | WEIGHT % |
| --- | --- |
| Petrolatum | 18.50 |
| Cyclomethicone | 41.50 |
| Iron Powder/Charcoal (5:1 weight ratio) | 30.00 |
| Dihydroxyacetone | 5.00 |
| Water | 4.00 |
| Cetyl Dimethicone Copolyol | 1.00 |

Activation of this system is achieved by wetting the face with aerated water prior to application of the sunless tanning agent. A warm sensation occurs through operation of the redox system while the dihydroxyacetone bronzes the skin. By this treatment the consumer has the combined aesthetic feel of sunshine warmth and the resultant color of a natural tan all without being exposed to harmful ultraviolet radiation.

EXAMPLE 4

Illustrated here is a shampoo incorporating the redox system of the present invention. Table IV lists the shampoo composition.

TABLE IV

| COMPONENT | WEIGHT % |
| --- | --- |
| Sodium Lauryl Ether Sulfate | 16.00 |
| Cocoamidopropylbetaine | 2.00 |
| Silicone Microemulsion | 4.00 |
| Jaguar C13S | 0.10 |
| Ethylene Glycol Distearate | 2.00 |
| Fragrance | 1.00 |
| Iron Powder/Charcoal (10:1 weight ratio) | 10.00 |
| Polyethylene Glycol 200 | Balance |

The above shampoo concentrate is delivered to the hair and wetted. Heat and lather are generated by the addition of a small amount of water. The consumer feels the aesthetic pleasure of warmth onto the scalp and foam providing good skinfeel to the fingers as the head is being massaged. The head is then rinsed clear of the composition. Shampoo may be reapplied for a second round followed again by rinsing.

EXAMPLE 5

This Example illustrates a shaving cream according to the present invention. Table V lists components of the self-heating shaving cream.

TABLE V

| COMPONENT | WEIGHT % |
| --- | --- |
| PHASE A | |
| Cetyl Alcohol | 30.00 |
| Glycerin | 15.00 |
| Iron/Charcoal (4:1 weight ratio) | 20.00 |
| PEG 40 Diisostearate | 1.00 |
| PHASE B | |
| Propylene Glycol | 15.00 |
| Preservative | 1.00 |
| Triethanolamine | 1.00 |
| Water | Balance |

The foregoing description and examples illustrate selected embodiments of the present invention. In light thereof variations and modifications will be suggested to one skilled in the art, all of which are within the spirit and purview of this invention.

What is claimed is:

1. A self-warming composition comprising:
   (i) from about 0.1 to about 30% by weight of silicone oil or carboxylic ester as a skin conditioning agent; and
   (ii) from about 1 to about 95% by weight of a redox system based upon iron powder and a high surface area catalyst which is charcoal.

2. A self-warming composition comprising:
   (i) from about 0.5 to about 30% by weight of a skin conditioning agent which is a humectant selected from the group consisting of propylene glycol, dipropylene glycol, polypropylene glycol, sorbitol, hydroxypropyl sorbitol, hexylene glycol, 1,3-butylene glycol, 1,2,6-hexane triol and mixtures thereof; and
   (ii) from about 1 to about 95% by weight of a redox system based upon iron powder and a high surface area catalyst which is charcoal.

3. A self-warming composition comprising:
   (i) from about 0.001 to about 10% by weight of a skin conditioning agent which is a keratolytic agent selected from the group consisting of $C_2$–$C_{25}$ alpha-hydroxy carboxylic acid, beta-hydroxy carboxylic acid and salts thereof; and
   (ii) from about 1 to about 95% by weight of a redox system based upon iron powder and a high surface area catalyst which is charcoal.

4. A self-warming composition comprising:
   (i) from about 0.1 to about 15% by weight of dihydroxyacetone as a skin conditioning agent; and
   (ii) from about 1 to about 95% by weight of a redox system based upon iron powder and a high surface area catalyst which is charcoal.

5. The composition according to claim 1 wherein the iron powder and catalyst are present in a weight ratio of about 1000:1 to about 1:1000.

6. The composition according to claim 5 wherein the weight ratio is about 10:1 to about 2:1.

7. The composition according to claim 3 wherein the keratolytic agent is selected from the group consisting of glycolic acid, lactic acid, salicylic acid and mixtures thereof.

* * * * *